(12) United States Patent
Chou et al.

(10) Patent No.: US 9,962,687 B1
(45) Date of Patent: May 8, 2018

(54) LOW CARBON FOOTPRINT PROCESS FOR REGENERATING SULFURIC ACID AND RECOVERING HYDROCARBONS FROM A SPENT SULFURIC ACID CATALYST FROM AN ALKYLATION UNIT

(71) Applicants: Chao-Shan Chou, Tainan (TW); Tse-Chuan Chou, Tainan (TW)

(72) Inventors: Chao-Shan Chou, Tainan (TW); Tse-Chuan Chou, Tainan (TW)

( * ) Notice: Subject to any disclaimer, the term of this patent is extended or adjusted under 35 U.S.C. 154(b) by 0 days. days.

(21) Appl. No.: 15/633,857

(22) Filed: Jun. 27, 2017

(51) Int. Cl.
  B01J 27/30 (2006.01)
  C07C 2/62 (2006.01)
  C07C 7/144 (2006.01)
(52) U.S. Cl.
  CPC ............ *B01J 27/30* (2013.01); *C07C 2/62* (2013.01); *C07C 7/144* (2013.01); *C07C 2527/054* (2013.01)

(58) Field of Classification Search
  None
  See application file for complete search history.

(56) References Cited

U.S. PATENT DOCUMENTS

| | | | | |
|---|---|---|---|---|
| 4,570,027 A | * | 2/1986 | Boucher | B01J 29/084 502/79 |
| 5,275,738 A | * | 1/1994 | Salinaro | B01D 65/102 210/321.6 |
| 5,547,655 A | * | 8/1996 | Chou | C01B 17/92 204/157.15 |
| 5,888,920 A | * | 3/1999 | Chou | B01J 27/30 208/13 |
| 8,114,802 B2 | * | 2/2012 | Odueyungbo | B01D 61/142 208/305 |
| 2007/0272614 A1 | * | 11/2007 | Minhas | B01D 61/246 210/651 |

* cited by examiner

*Primary Examiner* — Tam M Nguyen
(74) *Attorney, Agent, or Firm* — Bacon & Thomas, PLLC

(57) ABSTRACT

A method for regenerating a spent sulfuric acid catalyst and recovering hydrocarbons from a spent sulfuric acid catalyst from alkylation of olefins and alkanes by using a hydrophobic supported liquid membrane is provided.

6 Claims, 2 Drawing Sheets

LOW CARBON FOOTPRINT PROCESS FOR REGENERATING SULFURIC ACID AND RECOVERING HYDROCARBONS FROM A SPENT SULFURIC ACID CATALYST FROM AN ALKYLATION UNIT

FIELD OF THE INVENTION

The present invention is related to a method of regeneration of a spent sulfuric acid catalyst and recovery of hydrocarbons from a spent sulfuric acid catalyst from alkylation of olefins and alkanes via using of a hydrophobic supported liquid membrane.

BACKGROUND OF THE INVENTION

In U.S. Pat. No. 5,547,655, the inventors of the present invention disclose an electrochemical process for recovery and regeneration of sulfuric acid from the spent sulfuric add catalyst of the alkylation of C3-C5 olefins and alkanes by using active intermediates generated by electrolysis, heat and photolysis. Both the organic impurities and water containing in the spent sulfuric acid catalyst are simultaneously removed under mild operating conditions. Over 90% water and 95% organic impurities of its initial value, respectively, are efficiently removed from the spent sulfuric acid catalyst, which avoids the disadvantages of the combustion of the corrosive spent sulfuric acid catalyst at high temperature, the purification and oxidation of $SO_2$ at high temperature in the traditionally commercialized process. In U.S. Pat. No. 5,547,655, the organic impurities in the spent sulfuric acid catalyst are decomposed mainly to $CO_2$ and $H_2O$, and thus it is not a low carbon footprint process.

In U.S. Pat. No. 5,888,920, the inventors of the present invention disclose a continuous integrated process for in situ regenerating sulfuric acid from an alkylation unit and recycling the regenerated sulfuric add as a catalyst to the alkylation unit. Similar to U.S. Pat. No. 5,547,655, the organic impurities in the spent sulfuric acid catalyst are decomposed mainly to $CO_2$ and $H_2O$, and thus it is not a low carbon footprint process.

SUMMARY OF THE INVENTION

A primary objective of the present invention is to provide an improvement to the electrochemical process disclosed in U.S. Pat. No. 5,547,655 and U.S. Pat. No. 5,888,920, which reduces the carbon footprint by recovering hydrocarbons and recycling alkyl sulfates contained in the spent sulfuric acid catalyst via using a hydrophobic supported liquid membrane.

Preferred embodiments of the present invention includes (but not limited to) the following items:
1. A continuous low carbon footprint process for regenerating sulfuric acid and recovering hydrocarbons from a spent sulfuric acid catalyst from an alkylation unit, comprising the following steps:
   (a) withdrawing from said alkylation unit an alkylation effluent comprising the spent sulfuric acid catalyst comprising sulfuric acid, micelles of alkyl sulfates with hydrocarbons embedded therein, and water; gaseous hydrocarbons and liquid hydrocarbons;
   (b) separating said alkylation effluent into said spent sulfuric acid catalyst, said gaseous hydrocarbons and said liquid hydrocarbons;
   (c) simultaneously passing said spent sulfuric acid catalyst and a portion of said liquid hydrocarbons from step (b) or an alkylate product through a feeding side and a stripping side of a hydrophobic supported liquid membrane device, respectively, wherein said device comprises a hydrophobic supported liquid membrane separating the stripping side and the feeding side, and said hydrophobic supported liquid membrane comprises nanopores or micropores filled with the liquid hydrocarbons or the alkylate product, so that said hydrocarbons embedded in the micelles in the spent sulfuric acid catalyst in the feeding side diffuses through said hydrophobic supported liquid membrane to said liquid hydrocarbons or said alkylate product, and thus obtaining a liquid hydrocarbon stream or an alkylate product stream with recovered hydrocarbons, and a spent sulfuric acid stream with less hydrocarbons; and
   (d) regenerating said spent sulfuric acid stream with less hydrocarbons from step (c), which comprises removing water from said spent sulfuric acid stream.
2. The process of Item 1 further comprising the following steps:
   (e) passing said gaseous hydrocarbons and said liquid hydrocarbons from step (b) and said liquid hydrocarbon stream or said alkylate product stream with recovered hydrocarbons from step (c) to a fractionator;
   (f) recycling at least a portion of the regenerated sulfuric acid from step (d) to said alkylation unit.
3. The process of Item 1, wherein said regenerating in step (d) comprises contacting said spent sulfuric acid stream with less hydrocarbons from step (c) with a nanoporous or microporous hydrophilic membrane, so that water therein diffuses into nanopores or micropores of the nanoporous or microporous hydrophilic membrane; and passing dry air over the nanoporous or microporous hydrophilic membrane, so that water in the nanopores or micropores of the nanoporous or microporous hydrophilic membrane evaporates, and is carried away by the flowing dry air.
4. The process of Item 1, wherein said regenerating in step (d) comprises heating said spent sulfuric acid stream with less hydrocarbons from step (c), so that water therein evaporates.
5. The process of Item 1, wherein the spent sulfuric add catalyst in step (b) has a concentration of 85-97 wt % of sulfuric acid, and a regenerated sulfuric acid from step (d) has a concentration of 90-98 wt % of sulfuric acid.
6. The process of Item 1, wherein said spent sulfuric acid catalyst passes through the feeding side and said liquid hydrocarbons or alkylate product passes through the shell side of the hydrophobic supported liquid membrane device countercurrently in step (c).

The spent sulfuric acid catalyst contains impurities of water and micelles of alkyl sulfates with hydrocarbons embedded therein, wherein the alkyl sulfates are useful intermediates in the alkylation of C3-C5 olefins and alkanes, and thus it is desirable to keep the alkyl sulfates in the regenerated sulfuric acid. In the present invention, hydrocarbons embedded in the micelles are recovered by using the hydrophobic supported liquid membrane, followed by removal of water, and thus obtain a regenerated sulfuric acid with most of the hydrocarbons and water being removed therefrom, and with the alkyl sulfates remaining therein. The hydrocarbons recovered from the spent sulfuric acid catalyst can be introduced to a fractionator for recovery of unreacted alkanes and olefins, and alkylated hydrocarbon product. Accordingly, the carbon footprint can be significantly reduced in the present invention in comparison with the processes disclosed in U.S. Pat. No. 5,547,655 and U.S. Pat. No. 5,888,920.

DETAILED DESCRIPTION OF THE INVENTION

Based on the hydrophobic properties of hydrocarbons of C3-C5 olefins and alkanes and alkylate products, and hydrophilic properties of sulfuric acid and water, direct dissolution of hydrocarbons in the sulfuric acid and water phase is negligible in comparison with the dissolution of hydrocarbons of organic impurities embedded in the cores of aggregated alkyl sulfate micelles in the sulfuric acid and water phase, i.e. the hydrocarbons dissolved in the sulfuric acid and water phase are mainly embedded in the cores of the alkyl sulfate micelles.

In general, producing one ton gasoline makes 0.1 ton spent sulfuric acid catalyst. If ten thousand barrels of gasoline are produced per day, one hundred tons of spent sulfuric acid catalyst are produced. The amount of hydrocarbons embedded in the cores of alkyl sulfate micelles, for example, by using butylene as olefin feed is 60 wt % (2.7 tons) of the 4.5 wt % organic impurities (4.5 tons) in the spent sulfuric acid. 2.43 tons of hydrocarbons will be recovered from the one hundred tons of spent sulfuric acid catalyst, assuming a hydrophobic supported liquid membrane (HSLM) device used in the present invention has a 90% recovery efficiency; and 2.07 tons of alkyl sulfates which contains 0.27 tons (10%) unrecovered hydrocarbons will remain in by the regenerated spent sulfuric acid recycled to alkylation unit in the ten thousand barrels of gasoline production. The organic impurities in the spent sulfuric add catalyst are substantially recovered, resulting a low carbon footprint process which is operated at very mild conditions and low cost according to the present invention.

As will be described hereinafter in greater details, the essence of our invention includes an integrated low carbon footprint process which combines the alkylation unit and the regeneration of spent sulfuric acid unit. The regeneration of spent sulfuric acid unit combines two stages in series: one is the hydrophobic supported liquid membrane (HSLM) technique or device to recover the hydrocarbons in organic impurities in the spent sulfuric acid catalyst; and the other is the hydrophilic membrane (HM) device or the moving hydrophilic membrane (MHM) device to remove water from the hydrocarbon removed spent sulfuric acid catalyst. The regenerated sulfuric acid containing alkyl sulfates is recycled to the alkylation unit as the alkylation catalyst. The alkyl sulfates contained in the recycled sulfuric acid catalyst are further used to synthesize the alkylate product in the alkylation contactor reactor.

Figure 1A:
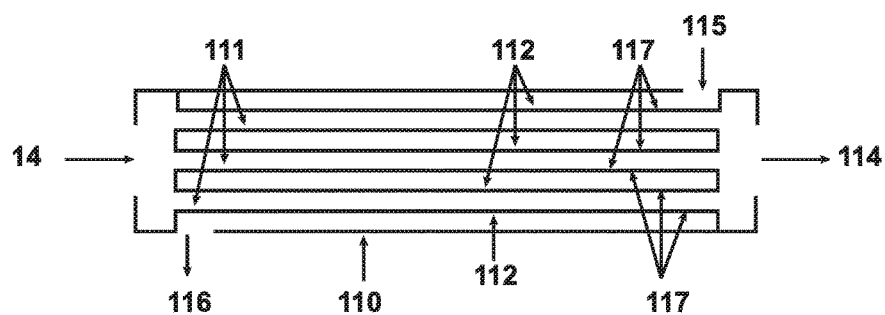
FIG. 1(a) is a schematic view showing a hydrophobic supported liquid membrane device for the recovery of hydrocarbons from organic impurities in a spent sulfuric acid catalyst from an alkylation unit.
Figure 1B:
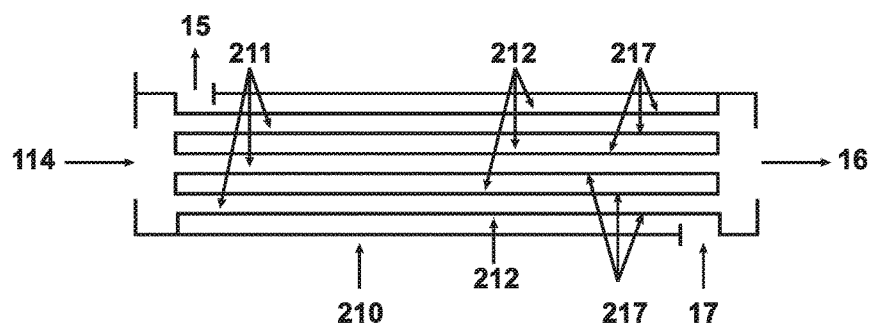
FIG. 1(b) is a schematic view showing a hydrophilic membrane device for the removal of water from the hydrocarbons recovered spent sulfuric acid catalyst from FIG. 1(a).
Figure 1C:
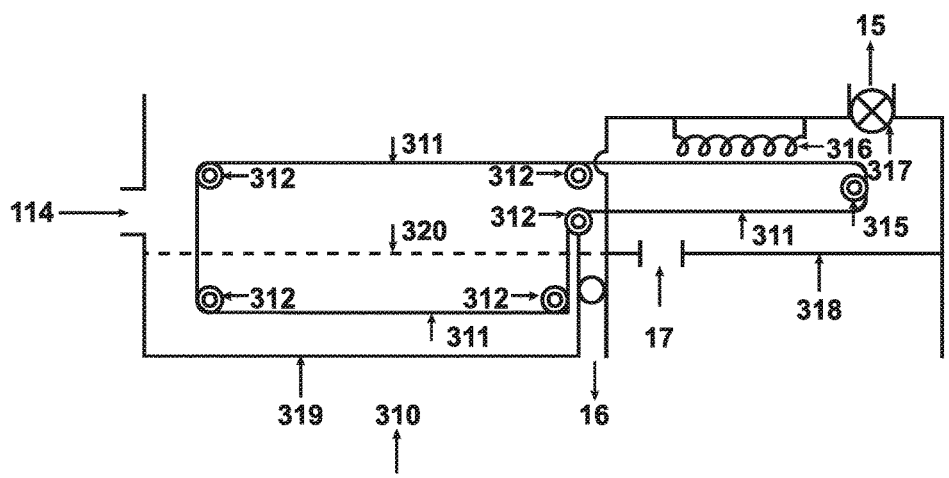
FIG. 1(c) is a schematic view showing a moving hydrophilic membrane device for the removal of water from the hydrocarbons recovered spent sulfuric acid catalyst from FIG. 1(a).

The drawings of FIG. 1(a) to 1(c) are regeneration units for the spent sulfuric acid catalyst from an alkylation process of olefins and isoparaffins. The regeneration unit shown in FIG. 1(a) is a hydrophobic supported liquid membrane (HSLM) device, which is used to recover hydrocarbons from the organic impurities in the spent sulfuric acid catalyst. The hydrocarbons recovered spent sulfuric acid catalyst, i.e. no or insignificant hydrocarbons and mainly dialkyl sulfates and monoalkyl hydrosulfates in the spent sulfuric acid catalyst, from the device shown in FIG. 1(a) is then introduced to a hydrophilic membrane (HM) device, as shown in FIG. 1(b), or a moving hydrophilic membrane (MHM) device, as shown in FIG. 1(c), where water is further removed.

As shown in FIG. 1(a), the spent sulfuric acid catalyst 14 from a settler or separator for an alkylation effluent in an alkylation process is fed into a tube side of the HSLM device 110, and a portion of a liquid alkylate product 115 is fed into the shell side of the HSLM device 110. The space 111 and space 112 are the tube side space and the shell side space, respectively, which are separated by a polytetrafluoroethylene (PTFE) microporous membrane 117. The PTFE microporous membrane 117 is hydrophobic and the liquid alkylate product is also hydrophobic, so that the micropores of the PTFE microporous membrane 117 are filled with the liquid alkylate product. The hydrocarbons of the organic impurities embedded in the cores of dialkyl sulfate micelles and monoalkyl hydrosulfate micelles in the spent sulfuric acid catalyst in the tube side space 111 are released from the micelles, which then dissolve in the liquid alkylate product at openings of the micropores, and diffuse through the micropores to the liquid alkylate product in the shell side space 117 mainly by two driving forces: (1) partition coefficient of hydrocarbons between the spent sulfuric acid catalyst and the liquid alkylate product; and (2) the concentration gradient of hydrocarbons within the micropores which are filled with the liquid alkylate product. The flow pattern in the HSLM device 110 of FIG. 1(a) is a countercurrent flow pattern, where hydrocarbons diffuse from the spent sulfuric acid catalyst 14 flowing left to right into the liquid alkylate product 115 flowing right to left, thereby obtaining a hydrocarbons recovered spent sulfuric acid catalyst 114 which is then fed to the second stage, i.e. a water removing device, the HM device 210 shown in FIG. 1(b) or the MHM device 310 shown in FIG. 1(c); and a hydrocarbon enriched liquid alkylate product 116 which is fed to a fractionator directly or after being joined with hydrocarbons from the settler or separator.

The hydrocarbons recovered spent sulfuric acid catalyst 114 contains sulfuric acid, dialkyl sulfates, monoalkyl hydrosulfates, water and no or insignificant hydrocarbons, which can be advantageously recycled to the alkylation process as a catalyst if the useful intermediates of dialkyl sulfates and monoalkyl hydrosulfates are kept therein and only water is removed therefrom. FIG. 1(b) shows a hydrophilic membrane (HM) device 210, which is similar to the the HSLM device 110 shown in FIG. 1(a) in structure and operation. In the HM device 210, the tube side space 211 and the shell side space 212 are separated by a nanoporous or microporous hydrophilic membrane 217, for example, Nafion®, which can selectively transfer water molecules through the nanopores or micropores in the membrane 217, when the hydrocarbons recovered spent sulfuric acid catalyst 114 flows left to right through the tube side space 211 and hot dry air 17 flows right to left through the shell side space 212. The moisture enriched air 15 exiting from the HM device 210 is introduced to an absorber for purification.

The regenerated sulfuric acid 16 containing dialkyl sulfates and monoalkyl hydrosulfates and substantially no water is recycled to the alkylation unit as the alkylation catalyst.

Alternatively, a moving hydrophilic membrane (MHM) device 310 shown in FIG. 1(*c*) can be used to remove water from the hydrocarbons recovered spent sulfuric acid catalyst 114. The MHM device 310 contains a spent sulfuric acid stored tank 319 and a dryer chamber 318. The hydrocarbons recovered spent sulfuric add catalyst 114 is introduced into the tank 319, which will exit from the tank 319 via an outlet at a predetermined liquid level 320. An endless loop of a nanoporous or microporous hydrophilic membrane 311 circulates around five rollers 312 by a motor driven roller 315, wherein two of the five rollers 312 are below the liquid level 320 and the remaining three rollers 312 are above the liquid level 320, and the motor driven roller 315 is in the dryer chamber 318, so that the membrane 311 will travel through the hydrocarbons recovered spent sulfuric acid catalyst 114 in the tank 319, in the dryer chamber 318, above the liquid level 20, and again into the hydrocarbons recovered spent sulfuric acid catalyst 114, and so on. A vacuum pump 317 and a heater 316 are installed in the dryer chamber 318, so that air 17 can flow through the dryer chamber 318 while being heated by the heater 316. The hydrocarbons recovered spent sulfuric acid catalyst 114 continuously flows into the tank 319, where water therein is removed by the moving hydrophilic membrane 311, and thus a regenerated sulfuric acid 16 containing dialkyl sulfates and monoalkyl hydrosulfates and substantially no water continuously exits from the tank 319, which can be recycled to the alkylation unit as the alkylation catalyst. The hydrophilic membrane 311 with absorbed water will leave the tank 319 and enter the dryer chamber 318, where the absorbed water evaporates and is carried away by the flowing heated air 17, thereby obtaining a regenerated hydrophilic membrane 311 to be returned to the tank 319. At the same time, a moisture enriched air 15 flows out from the dryer chamber 318, which can be treated by an absorber.

Figure 2:
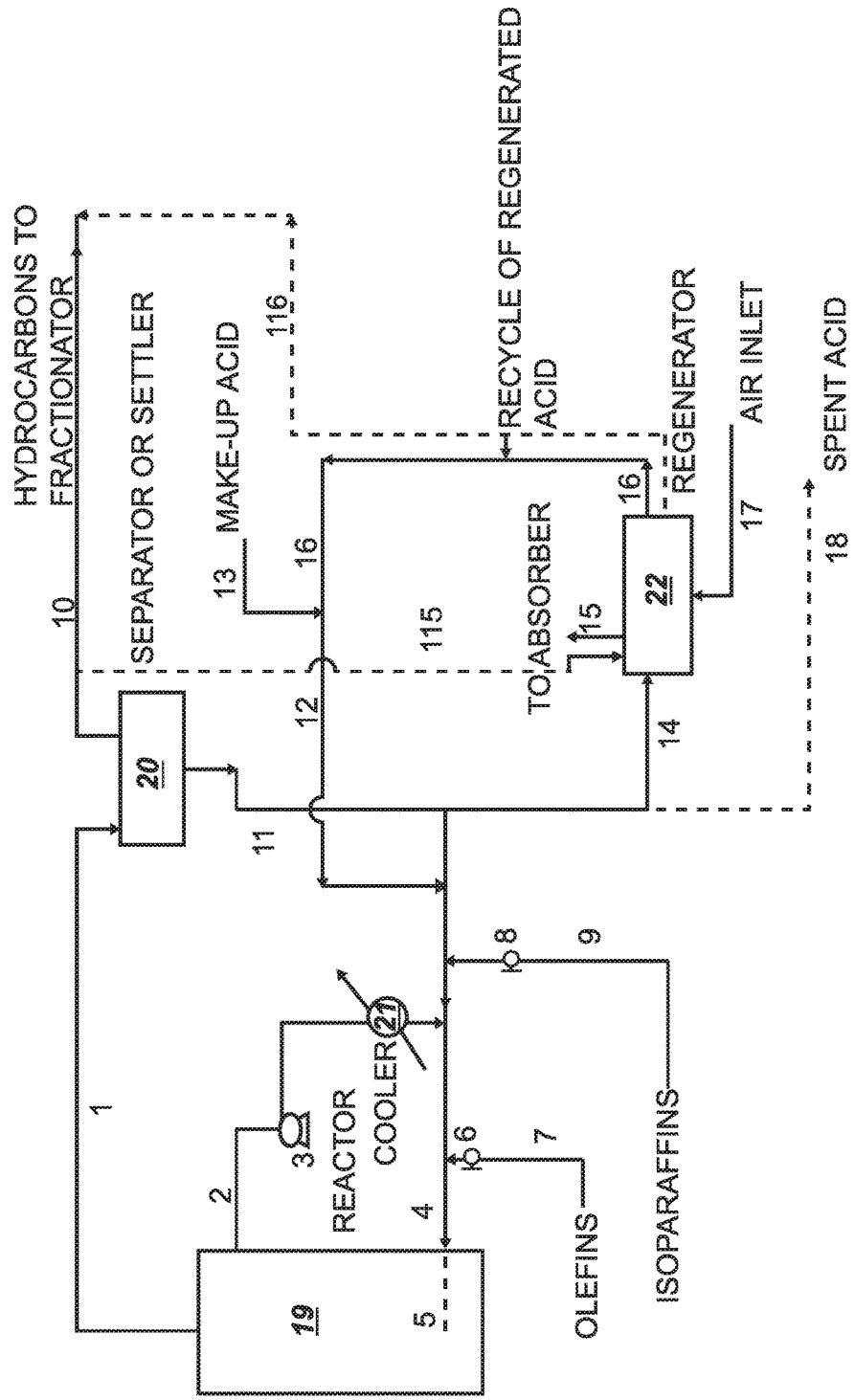
FIG. 2 is a schematic flowchart showing a low carbon footprint alkylation process integrated with a regenerator for a spent sulfuric acid catalyst.

A low carbon footprint integrated alkylation process including a manufacture process using concentrated sulfuric acid as catalyst and a regeneration process of spent sulfuric acid catalyst from this process according to one of the preferred embodiments in the present invention is shown in FIG. 2. As shown in FIG. 2, hydrocarbons of olefins and isoparaffins are fed via a line 7 and a line 9, respectively, into a conventional catalytic alkylation reactor 19, wherein a liquid catalyst such as sulfuric acid is introduced via a line 12. The flow rates of olefins and isopraffins are controlled by valves 6 and 8, respectively. The liquid catalyst intimately contacts the hydrocarbons through a distributor 5 in the reactor 19. The temperature of alkylation is controlled by circulation of a part of the reactants and products through a cooler 21 via a line 2 by a pump 3. At the end of the desired residence time in the alkylation reactor, an effluent from the alkylation reactor 19 is withdrawn and passed via a line 1 as a feed into a separator or settler 20.

In the separator or settler 20, the effluent from the alkylation reactor 19 is separated into a hydrocarbon portion which is passed via a line 10 to a fractionator, and a spent sulfuric acid portion which is withdrawn via a line 11. The spent sulfuric add in the line 11 is partially recycled to the alkylation reactor 19 via a line 4 if it is necessary, and is mainly passed to a regenerator 22 via a line 14.

The regenerator 22 containing the HSLM device 110 as shown in FIG. 1(*a*) and the HM device 210 as shown in FIG. 1(*b*) or the MHM device 310 as shown in FIG. 1(*c*) in series as described above. A portion of hydrocarbon in the line 10 or an alkylate product is passed to the regenerator 22 via a line 115 as a stripping stream, i.e. the hydrophobic liquid in the shell side space in the HSLM device to recover hydrocarbons in organic impurities in the spent sulfuric acid. The hydrocarbons recovered stripping stream is recycled and passed to the fractionator via a line 116. Sometimes, a portion of the spent sulfuric acid is withdrawn via a line 18 as a purge stream. A stripping dry air inlet is introduced to the regenerator 22 via a line 17 for removing water from the hydrophilic membrane, and a moisture enriched air exiting from the regenerator 22 is sent via a line 15 to an absorber (not shown). A regenerated sulfuric acid containing alkyl sulfates and substantially no water is recycled to the alkylation reactor 19 via a line 16 and the line 12. A make-up sulfuric acid is introduced into the alkylation reactor 19 via a line 13 and the line 12.

What is claimed is:

1. A continuous low carbon footprint process for regenerating sulfuric acid and recovering hydrocarbons from a spent sulfuric acid catalyst from an alkylation unit, comprising the following steps:
    (a) withdrawing from said alkylation unit an alkylation effluent comprising the spent sulfuric acid catalyst comprising sulfuric acid, micelles of alkyl sulfates with hydrocarbons embedded therein, and water; gaseous hydrocarbons and liquid hydrocarbons;
    (b) separating said alkylation effluent into said spent sulfuric acid catalyst, said gaseous hydrocarbons and said liquid hydrocarbons;
    (c) simultaneously passing said spent sulfuric acid catalyst and a portion of said liquid hydrocarbons from step (b) or an alkylate product through a feeding side and a stripping side of a hydrophobic supported liquid membrane device, respectively, wherein said device comprises a hydrophobic supported liquid membrane separating the stripping side and the feeding side, and said hydrophobic supported liquid membrane comprises nanopores or micropores filled with the liquid hydrocarbons or the alkylate product, so that said hydrocarbons embedded in the micelles in the spent sulfuric acid catalyst in the feeding side diffuses through said hydrophobic supported liquid membrane to said liquid hydrocarbons or said alkylate product, and thus obtaining a liquid hydrocarbon stream or an alkylate product stream with recovered hydrocarbons, and a spent sulfuric acid stream with less hydrocarbons; and
    (d) regenerating said spent sulfuric acid stream with less hydrocarbons from step (c), which comprises removing water from said spent sulfuric acid stream.

2. The process of claim 1 further comprising the following steps:
    (e) passing said gaseous hydrocarbons and said liquid hydrocarbons from step (b) and said liquid hydrocarbon stream or said alkylate product stream with recovered hydrocarbons from step (c) to a fractionator;
    (f) recycling at least a portion of the regenerated sulfuric acid from step (d) to said alkylation unit.

3. The process of claim 1, wherein said regenerating in step (d) comprises contacting said spent sulfuric acid stream with less hydrocarbons from step (c) with a nanoporous or microporous hydrophilic membrane, so that water therein diffuses into nanopores or micropores of the nanoporous or microporous hydrophilic membrane; and passing dry air over the nanoporous or microporous hydrophilic membrane, so that water in the nanopores or micropores of the nanoporous or microporous hydrophilic membrane evaporates, and is carried away by the flowing dry air.

4. The process of claim 1, wherein said regenerating in step (d) comprises heating said spent sulfuric add stream with less hydrocarbons from step (c), so that water therein evaporates.

5. The process of claim 1, wherein the spent sulfuric acid catalyst in step (b) has a concentration of 85-97 wt % of sulfuric acid, and a regenerated sulfuric acid from step (d) has a concentration of 90-98 wt % of sulfuric acid.

6. The process of claim 1, wherein said spent sulfuric acid catalyst passes through the feeding side and said liquid hydrocarbons or alkylate product passes through the shell side of the hydrophobic supported liquid membrane device countercurrently in step (c).

\* \* \* \* \*